US005520630A

United States Patent [19]
Daneshvar

[11] Patent Number: 5,520,630
[45] Date of Patent: May 28, 1996

[54] E-Z LEG SUPPORTS

[76] Inventor: Yousef Daneshvar, 21459 Woodfarm, Northville, Mich. 48167

[21] Appl. No.: 194,903

[22] Filed: Feb. 14, 1994

[51] Int. Cl.⁶ ........................................ A61F 13/00
[52] U.S. Cl. ........................ 602/60; 128/DIG. 15
[58] Field of Search ....................... 602/60, 62, 63, 602/1, 23, 26, 64, 65, 75; 128/DIG. 15

[56] References Cited

U.S. PATENT DOCUMENTS

| | | | |
|---|---|---|---|
| 366,590 | 7/1887 | Lubin | 602/60 |
| 3,138,156 | 6/1964 | Crowell et al. | 602/62 X |
| 3,209,517 | 10/1965 | Hyman | 602/62 X |
| 3,529,601 | 9/1970 | Kirkland | 602/60 X |
| 3,789,842 | 2/1974 | Froimson | 602/62 |
| 3,856,008 | 12/1974 | Fowler et al. | 128/DIG. 15 X |
| 3,933,150 | 1/1976 | Kaplan et al. | 128/DIG. 15 X |
| 4,146,021 | 3/1979 | Brosseau et al. | 602/62 X |

FOREIGN PATENT DOCUMENTS

| | | | |
|---|---|---|---|
| 498062 | 8/1992 | European Pat. Off. | 602/60 |
| 86/04811 | 8/1986 | WIPO | 602/63 |

*Primary Examiner*—Sam Rimell

[57] ABSTRACT

This invention introduces special types of pressure stockings that are easier to be used and use different techniques of bringing the edges or the body of these supports together, so that it will be easier for a patient to use them on a daily basis or for a pregnant person to put them on while tolerating the difficulties of pregnancy.

3 Claims, 5 Drawing Sheets

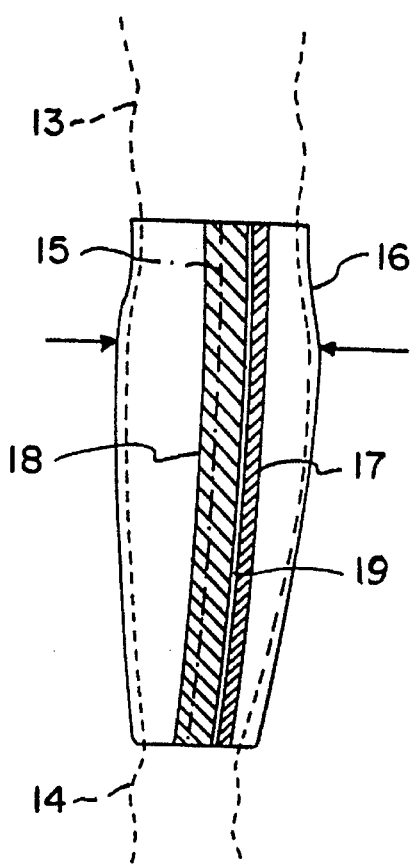
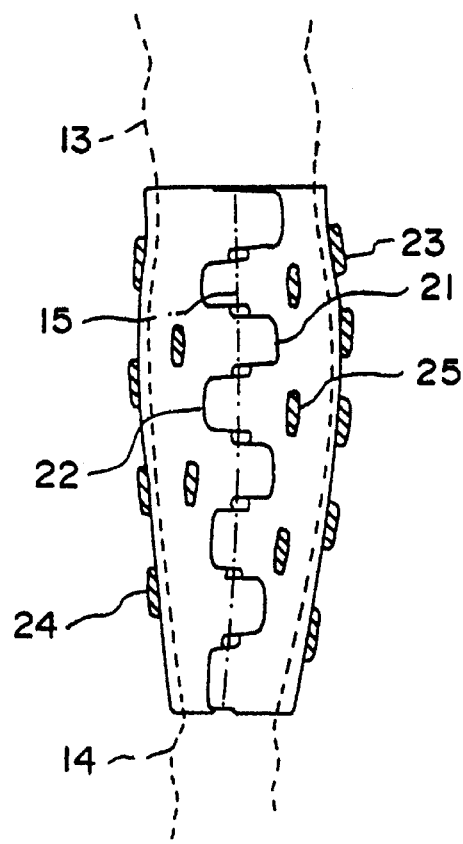
FIG. 3
FIG. 5
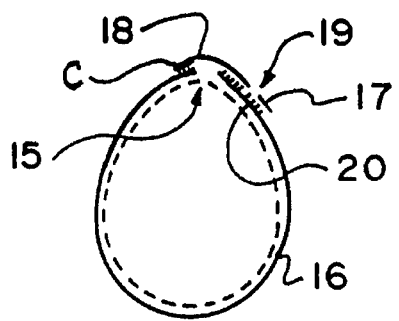
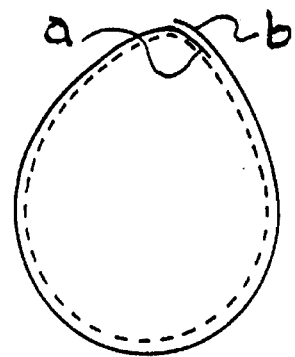
FIG. 4
FIG. 5A

E-Z LEG SUPPORTS

BACKGROUND OF THE INVENTION

The problem of fluid retention and swelling in the legs is common and is due to multiple problems such as Varicose veins, vascular incompetence and other problems such as pregnancy, etc. One mode of prevention and treatment for these conditions is to use pressure stockings. However, putting such stockings on the legs is not easy and requires significant daily effort and help so that many people would not or can not use them. This invention introduces new models and means that will make this job easier.

SUMMARY OF THE INVENTION

This invention introduces special types of pressure stockings that are much easier to be worn and taken off, therefore it will be helpful in many conditions in which they are required. In these models the units will utilize different models of pressure stockings that are easily handled: in one model an elastic sleeve of Velcro TM will be used to match and stick to a band of Velcro TM on the base of stocking to make a roll and allow easy rolling of this unit up and down. In another model the unit will use long strips or flaps covered by Velcro TM that will be properly placed on stockings to allow the stocking to be put on easily. These units can be modified to allow stimulation of the leg muscles with use of various stimulators.

The figures:

BRIEF DESCRIPTION OF THE FIGURES

The brief explanation of the figures:

FIG. 3. This shows an alternative way of holding the sides of the support stocking together.

FIG. 4. This shows a cross cut view of the unit shown in previous figure of 3.

FIG. 5. This shows a prototype unit which will wrap around the calf and be secured by a series of flaps or tongues.

FIG. 5A. This is to show the flap (a) under the connection area.

DETAILED DESCRIPTION OF THE INVENTION

Figure 1:
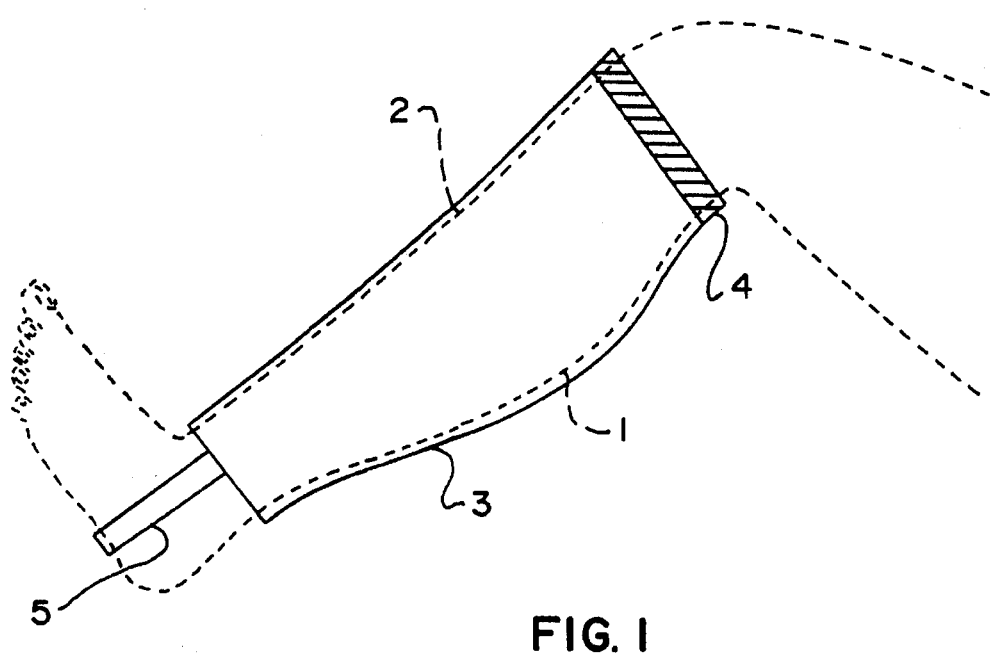
FIG. 1. This shows a general view of a patient using a prototype of these support units.

FIG. 1. This shows a general view of a patient using a prototype of these support units. In this figure the leg of the patient is shown with a dotted line and the shin is marked at 2 and the rear part of the calf at 1. In this figure no 3 shows the body of the elastic stocking, and no 4 shows a band which is made from the soft part of the Velcro TM "the loop" kind. As it is mentioned in the text, this will be elastic and expandable, so that it would not be damaged when is stretched during upward motion from the larger part of the calf or so. This figure also shows an optional band of 5 that will prevent the stocking from being pulled up more than it is intended to.

Figure 2:
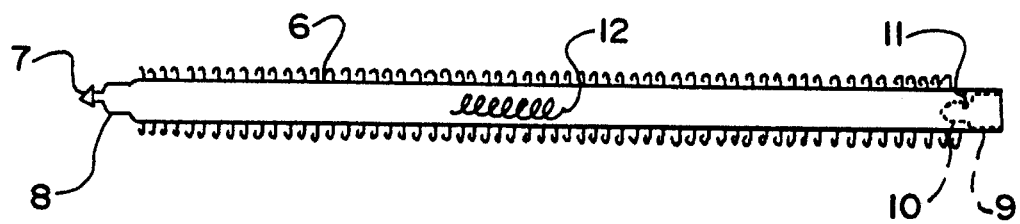
FIG. 2. This shows a unit that will stick to no 4 from previous figure and allow it to be removed easily.

FIG. 2. This is a schematic view to show the general make up of a unit that is to be used with the stocking mentioned in previous figure of 1. This unit is basically an elastic round piece covered or made up of "The Hook" kind of Velcro TM. This piece has a body shown at 6 which is like a rod covered by velcro and has end pieces of 8 and 9 that will allow them to fit each other easily in order to made an elastic velcro ring. In this figure the end 8 with its tip 7 is shown and it will fit the end 9 from the other end of this unit, so that the tip 7 will fit into the space 10. No 11 is to schematically show a small piece that will allow the tip 7 to be engaged and held tightly within space 10 until the small button of 11 is pressed to release the ends. Again, after the engagement of the ends this unit will be like a round, soft ring covered by a hook kind Velcro TM.

Figure 2A:
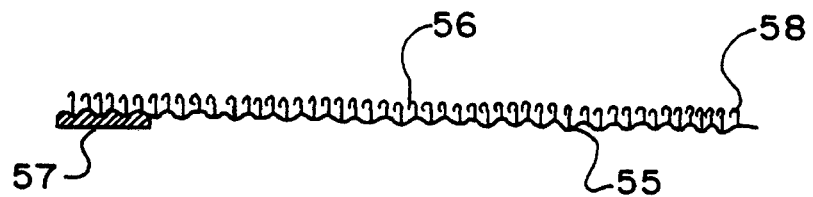
FIG. 2A. This shows an elastic band covered with "The Hook" kind of Velcro TM.

FIG. 2A. This shows the cross cut of an elastic band marked at 55 that is covered or made of "The Hook" kind of Velcro TM marked at 56. This piece will have the capacity of being stretched or pulled without being damaged. One end of this unit 57 has the soft part of the Velcro TM that will allow the piece 58 to stick to it if the band needed to be pulled too much. This piece is to be used and stuck on the band 4 of supportive stocking shown at FIG. 1. It is to allow the tension of the base of this stocking to be controlled.

FIG. 3. This figure shows a general view of an alternative way of holding the sides of the support stocking together. Except in this model the front of the unit will be open and needs to be held together. This unit will also be made from an elastic material that will make up the body of the unit. However, its sides or the front borders will be brought together and held properly in the front or sides by the use of a special Velcro TM band. This Velcro TM band 18 will be made to be sewn to one side of this stocking support such as the inner side (shown at point c FIG. 4) of the stocking and then to be stuck on the other side (band 20 FIG. 4) from the outer side of the stocking (shown at 16 FIG. 4). Importantly, in order to have a guide line of where this soft Velcro TM band of 18 should be slicked, another band of 17 shown in FIG. 3 and 4 will also be stuck over the outer side of the stocking 16 in order to show the limit of this engagement (like a guide line) so the inner border of the Velcro TM patch of 17 (clove to open line 19) will help in this regard. These two pieces of 18 and 17 can be placed over the piece 20 from the other side at the time of first use of this stocking so that later the piece 17 will be left in place to show the limit of the attachment of the piece 18. With a change in the patient's condition, the piece 17 may be moved inner or outer than its original position. Basically, the piece 18 will be fixed on the outer surface of the inner part of the stocking while piece 17 will be removably stuck to the other side to function as a guide line for piece 18. In this figure the leg of the patient is shown at the dotted line and the shin line is marked at 15 and shown with a dot and dash line. The inner knee is marked at 13 and the inner ankle at 14. The body of the stocking is marked at 16 and the Velcro TM band of 18 is shown with the piece of 17 standing parallel to it. The open line 19 shows the open guideline border between the piece 18 and 17. Importantly the lower end of this support unit may be a continuous circular piece (not to have a cut in front) to stay in the area above the ankle securely and to allow the person to place the rest of this unit in place.

Figure 6:
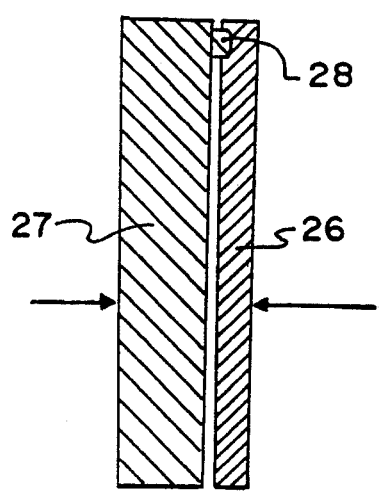
FIG. 6. This shows the piece a unit to make a support shown in figure of 3 & 4.
Figure 7:
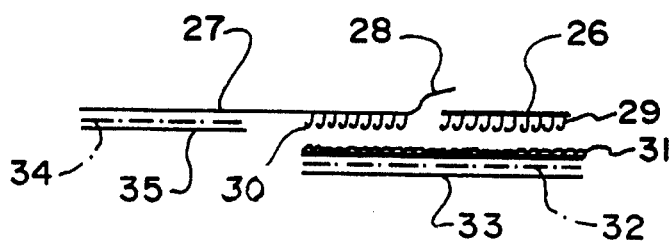
FIG. 7. This shows the cross cut view of the pieces shown in previous figure of 6.

FIG. 4. This figure shows a cross cut view of the unit shown in previous figure of 3. from a mid-calf position. This figure shows the border of the calf with a dotted line and the body of the stocking at 16. The sides of the stocking come and stand next to each other in the shin line area in front. The Velcro TM piece 18 which is fixed to the inner border of the stocking 16 at point c moves over the shin line of 15 to stick on the Velcro TM patch 20 which is fixed on the outer surface of the other border of the stocking 16. The piece 17 is also stuck on the outer surface of the Velcro TM patch 20 from stocking 16. The position of piece 17 may be changed if needed. It should be mentioned that the use of piece 17 is optional and is only to function as a guide line and the unit can be used without it, although it may be hard for the patient to remember where to stick the Velcro TM 18 on the outer side. No 19 shows an open line between the Velcro TM 17 and 18. The piece that helps to make such unit is shown at FIG. 6 & 7. Also, importantly these units may also have a long flap of elastic material or something soft (as shown at a from FIG. 5A) in order to overlap and stand under the open line between the borders of the elastic material in order to prevent any uncomfortable feeling or problem due to the connection part touching the skin.

Figure 8:
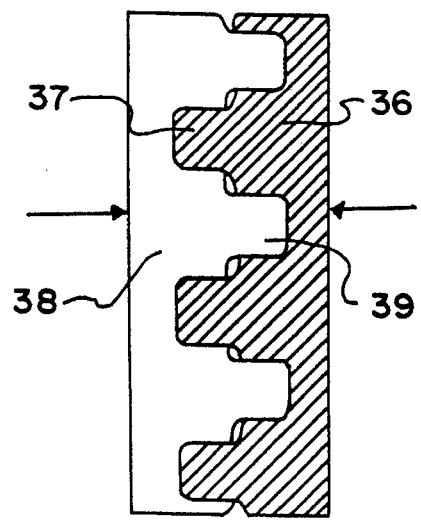
FIG. 8. This shows the piece that will be used to make the unit shown in previous figure of 5.
Figure 9:
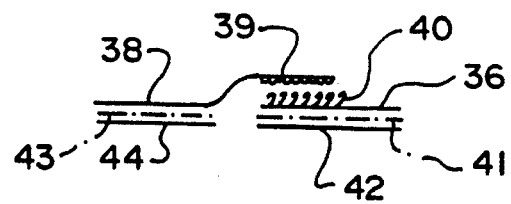
FIG. 9. This shows the cross cut of the piece shown in previous figure of 8.

FIG. 5. This figure shows a general view of a patient using a prototype unit; in this view the body of the support part will wrap around the rear part of the calf and the sides are to be held in place and secured by a series of flaps or tongues (such as no 21 & 22) that will alternatively go from one side to another in order to hold the unit in place. The body of this unit will be cut properly and then this front piece will be fixed on it. Importantly this front piece may be made separate (as shown in FIG. 8 & 9) in order to allow it to be mounted or fixed in the body of the unit (the elastic material) easily, so that it will be easy to sew it on or to glue it on in manufacturing. Importantly this figure also shows that this unit has a series of tabs that are to allow the adjustments to be made easily. In this figure this unit is on the calf of a patient. It has the flaps of 21 and 22 as an example of such pieces. Each one goes from one side to another. Importantly the lower end of this unit may also be circular to be pulled to stay in the area above the ankle securely so the person could hold one of each one of these flaps and pull them and stick them to the sides from the lower leg to the upper part and finally to have the whole unit in place. The area under these flaps will have a matching Velcro TM part as well. In this figure the inner knee is again shown at 13 and the inner ankle at 14 and the shin at 15. Some of the tabs are shown at 23, 24 and 25 and these are to allow the body of the stocking to be pulled up easily. The length, width, thickness, size, nature and the other characteristics of these tabs will vary.

FIG. 5A. This figure is a schematic view of the cross cut of the leg in the upper calf area, in order to show the extended flap or lining that goes beyond the line between the sides of this support stocking. In this view the calf is shown with a dotted line and the elastic support wraps around the calf to have one end of it b to overlap and go beyond the side of the other side shown at a. This is to prevent the inner side of the connection area made by Velcro TM from bothering the skin.

FIG. 6. This figure shows the piece that will be used to make the unit shown in previous figure of 3 & 4. This unit shows the two straps or bands of 27 and 26 next to each other. These pieces will have at least some part of their inner surface covered by Velcro TM, so it can stick over the matching part on the support stocking. In this figure also a small tab 28 which is to facilitate the removing of the piece 27 away from the stocking is shown.

FIG. 7. This figure shows the cross cut view of the pieces shown in previous figure of 6. In this figure the whole piece that can be fixed on the sides or borders of the properly shaped elastic material to make a support stocking is shown. In this figure the piece that will be sticked on the surface of the inner side or the border of the elastic piece is shown at 27 and the piece that will be fixed on the outer side or border of the elastic piece is shown at 31. The piece 27 has a film of adhesive shown with dot and dash at 34, protected by a layer of protective plastic 35 that will be peeled off prior to use. The piece 31 also has a film of adhesive shown with dot and dash at 32 and is protected by a layer of protective plastic 33 that will also be peeled off prior to use. The lower surface of the piece 27 will have a Velcro TM band shown at 30 that will be stuck to the outer surface of the matching piece 31. The piece 26 has a Velcro TM band shown at 29 that will be stuck to the matching piece of 31. The pieces 27 and 26 will be weakly glued to each other to allow these pieces to be placed on over the piece 31 next to each other properly at the first use. Then they will be separated and the piece 26 will play the role of a guide line for piece 27. The tape 28 is also shown. The process of fixing this unit on the support stocking can easily be done by the following method:

First the person will wear the regularly shaped support stocking.

Second this unit will be stuck on the outer surface of stocking in a proper place such as the shin line after peeling off the protective layers of 33 and 35.

Third the borders of the unit can be sown on the body of the stocking for more stability.

Forth the body of the support will be then cut along the center line.

FIG. 8. This figure shows the piece that will be used to make the unit shown in previous figure of 5. This unit has two straps of 36 and 38 connected to each other while one flap or a tongue of each one sticks to the outer surface of the other piece. For example, the tongue 37 from piece 36 is sticking to the outer surface of piece 38 (this area has a matching piece of Velcro TM) and the tongue 39 from piece 38 is sticking on side 36. This combination will make a sturdy unit, and will be easily handled as well. The inner surface of these tongue will stick to the other side by the use of Velcro TM. This unit will then be fixed on the borders of a properly shaped elastic piece to make a support stocking.

FIG. 9. This figure shows the cross cut view of the piece shown in previous figure of 8 in a line that passes through 38 and 39. This figure shows the cross cut view of the whole piece that can be fixed on the sides or borders of the properly shaped elastic material to make a support stocking by the mechanism mentioned earlier. In this figure the piece that will be stuck on the surface of the inner border of elastic piece is shown at 38 and the piece that will be fixed on the outer border of the elastic piece is shown at 36. The piece 38 has a film of adhesive shown with dot and dash at 43 protected by a layer of protective plastic 44 that will be peeled off prior to use. The piece 36 has also a film of adhesive shown with dot and dash at 41 and is protected by a layer of protective plastic 42 that will be peeled off prior to use. The lower surface of the piece 38 has a Velcro TM band shown at 39 that will be stuck to the outer surface of the matching area 40 from piece 36. The piece 36 has a Velcro TM band shown at 40. So in brief the pieces 38 and 36 will be fixed on the borders of the proper elastic piece to make the support stocking shown at FIG. 5. This can be easily done by the following method:

First the person will wear the regularly shaped support stocking.

Second this unit will be stuck on the outer surface of stocking in a proper place such as the shin line after peeling off the protective layers of 42 and 44.

Third the borders of the unit can be further sown on the body of the stocking for more stability.

Fourth the body of the support will then be cut along the center line.

Figure 10:
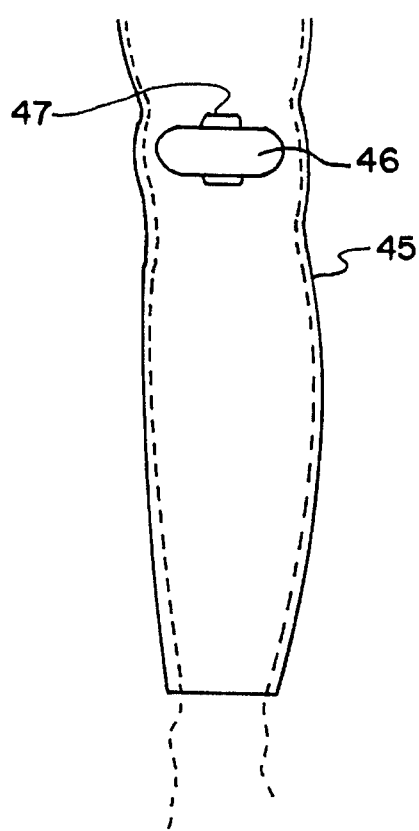
FIG. 10. This shows a model with an opening in the popliteal area.

FIG. 10. This figure shows the rear view of a model that has an opening in the popliteal area, in order to prevent the gathering of the wall of the stocking in this area when the person bends the knee. The gathering of thick material in this area is commonly bothersome and would pressure the vessels, nerve and tissue in that area. This opening will also allow some ventilation to occur as well. In this view the body of the unit is shown at 45 and the opening at 46. Also two tabs are shown: one in the upper side of the opening and another one in the bottom; only the upper tab is shown at 47.

Figure 11:
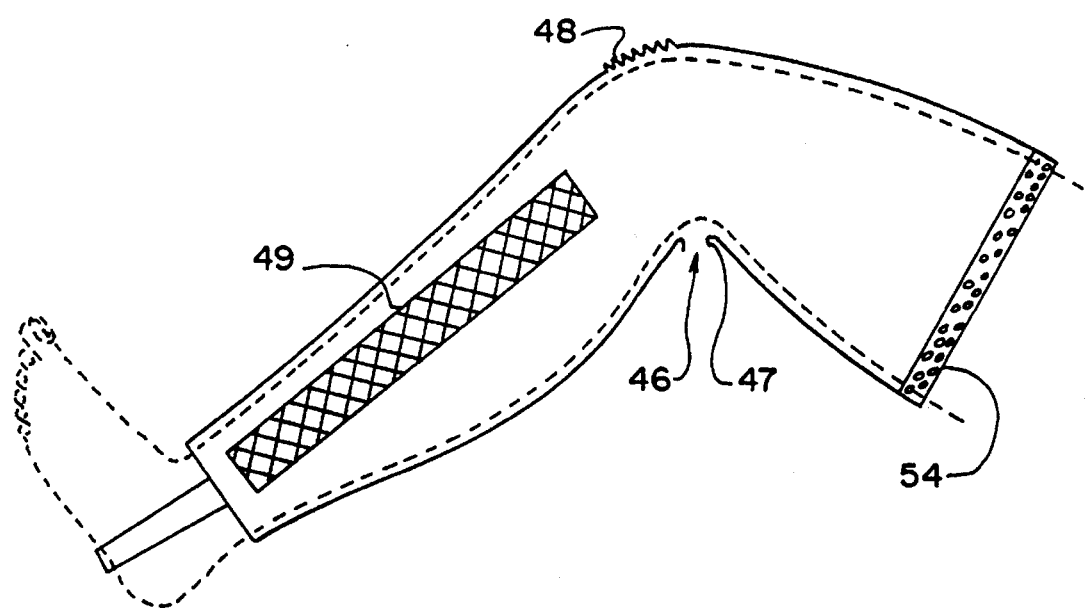
FIG. 11. This shows the side view of a model with a couple of the important improvement means.

FIG. 11. This figure shows the side view of a model that has a couple of the important means of these units. For example, in front of the knee this unit has an extra wall marked at 48 which is a patch like the wall of accordion, to allow the knee to bend without pulling the sides of the stocking and deform or weaken them. It also shows the opening in the popliteal area similar to the one shown in the previous figure of 10 which is to prevent the gathering of the wall of the unit in this area. This opening is shown at 46 and the tab is also shown at 47. Importantly the lateral side of this unit has the Velcro TM area marked at 49. This area will allow a second support unit to be wrapped around the leg and have its borders stuck to this area in order to give even more support which importantly is exchangeable and removeable. Such a patch may be placed on either side of this support or in any shape, number or location on the support that can be of benefit. This figure also shows the Velcro TM band of 54 that is elastic and will allow a matching piece of Velcro TM to be stuck to it in order to allow the tension of this area to be controlled for holding this unit in place as well as taking the unit off by the method mentioned in FIG. 1 and 2. This is an important and valuable option that will give significant comfort in use of this unit.

Figure 12:
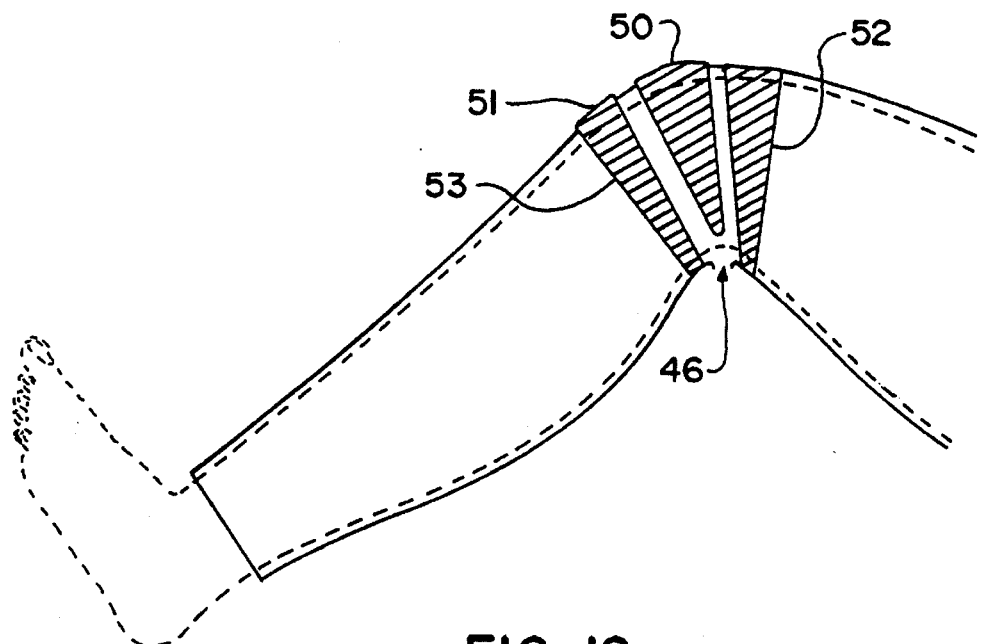
FIG. 12. This shows the side view of another model that has a series of supportive bands.

FIG. 12. This figure shows the side view of yet another model that has a series of supportive bands in the knee area in order to allow this unit to stabilize the knee joint more strongly and effectively. In this view three bands of stronger material are shown at 50, 51 and 52. The side of the unit shown at 51 is marked at 53. The special shape of these bands being wider in front and narrowed in the back will allow it to be functional during the function of this joint. When the joint is bent, it will separate these pieces from each other in front and they will get closer in the back. With the straightening of the knee, these pieces will come closer in the front and separate more in the back. This function will allow more support to the knee with much less discomfort. In this figure the opening 46 is also shown.

Figure 13:
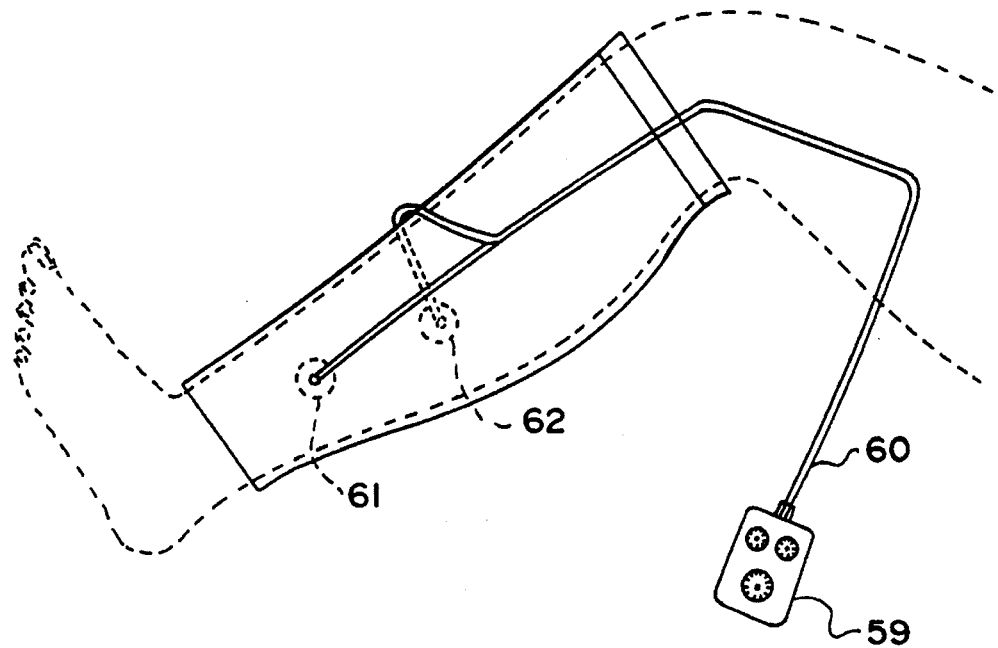
FIG. 13. This shows a unit that allows the legs to be stimulated to move.

FIG. 13. This is to show schematically the units that can be used for the stimulation of the muscles/nerves/tissues of the legs in order to have patients move their extremities and circulate the blood. In this figure a supportive stocking is shown that allows the patches of electrodes to be used and the electrodes wired properly with low profile and finally connected to a stimulator that is a minicomputer as well that allows proper changes to be made. In this figure the stimulator is shown at 59 and the wire system at 60 and the patches of electrodes at 61 and 62. These patches will allow electricity to be delivered to the proper part of the legs in order to cause the best result.

As a physician I have dealt with many different problems of life which I have observed in my patients. One of them is the significant problem with the retention of fluid and swelling of the legs. This is common and is basically due to the retention of fluid in the system due to many causes such as cardiac, renal or vascular problems such as Varicose veins or vascular insufficiency, after the removal of the veins in the legs etc. This condition also occurs during some of the normal events such as pregnancies, etc. Whatever the cause could be us doctors like to prevent significant edema in the legs and one method of treatment is to use pressure stockings on them. Unfortunately, the use of such units is not easy and putting them on the legs on and taking them off properly on a daily basis gets tiring and requires effort and help, so that in practice many people do not use them. Therefore, this inventor introduces this model that is easier to be used. In this model, basically a support stocking which more commonly will be made from a piece from the ankle area to the lower knee or above it will be used. This unit will be basically made from an elastic material that will be similar to the commonly used materials in this stocking. The degree of elasticity in different models may vary. This unit will have models that are:

A. Up to the lower knee and do not to go above the knee, or the below knee model.

B. The above knee model are not to be too long so that it would be close to the upper knee area.

C. A long unit to be long enough to reach the upper thigh area.

D. A unit that will be like panty hose.

In practice the patients will be able to chose a model they need.

These units will have a particular construction to allow them to be utilized. In one model the upper rim of the stocking will be made to have a rim made from the soft Velcro TM part. However, importantly this piece will be made elastic so that pulling it sideways would be possible and would not tear the piece apart. This piece will be placed in the upper outer surface of the upper rim. This piece has a couple of functions: first it will allow a matching piece of Velcro TM to be stuck on it in order to allow the tension of this piece to be controlled for holding this unit in place comfortably. This is an important and valuable option that will give significant comfort in use of this unit. Second, it will allow this unit to be removed easily with the use of a special piece shown at (FIG. 2). This piece is to be a long round elastic piece that will have endings that will fit each other in order to make a round elastic ring of about the size of the normal leg in the lower knee area. Except the outer part of this ring will be made from the hook part of the Velcro TM and therefore it can be stuck on the outer rim of the support mentioned above (shown at no 4 FIG. 1) due to the stickiness of the hook and the loop of the Velcro TM system. After the sticking of these two parts together, they will make a combined unit that will allow the stocking to be rolled down easily. At the time of putting the support stocking in place the reverse of this function will be done.

In another model B, the unit will use the same kind of elastic material except it will be made to have an open front that will be brought to each other by the use of a special technique. A prototype of this unit is shown at FIG. 3 and 4 and in this model a band of Velcro will be used to be stuck on the proper side such as in the shin line or close to it and along a straight line. This line will be chosen in the beginning of adjusting and making the unit. In the beginning the unit has to be properly measured and its extra materials are to be cut off then a patch similar to the one shown at FIG. 6 & 7 will be fixed on it by different means such as gluing, sewing etc. This will then make a unit that can be worn on the leg and would stick the velcro part 27 on the matching part from 31 to hold it in place securely. And then when it is to be taken off, the Velcro TM patch of 27 will be pulled away to allow the unit to be taken off.

In another model C, it will be basically similar to the model mentioned in Model A except it will have a zipper that will allow it to be closed.

Model D. This model will be similar to model B. except it also will also have a zipper that after the initial adjustment, will allow the unit to be worn on with its use. Still, the Velcro TM part may be used. The unit can be worn by putting the Velcro TM patches on.

In another model E, the unit will be very similar to the model B except in this model a series of Velcro TM flaps or tongues will be used to bring and hold the borders of the support unit together. This is shown at FIG. 5 and it can be made by combining a unit similar to the one shown at FIG. 8 and 9 to the borders of the elastic piece. This unit can be worn by holding these tongues and pulling them to the other side and sticking to the right part.

It is important to notice that a proper lining or flap will prevent the zipper from coming in touch with the skin and causing problem. One model of this is shown in FIG. 5A.

Some important factors will also be added to these units in order to cause further improvements such as following:

1. The outer part of these units may have a series of tabs that will allow the wall of the unit to be pulled away and adjusted. This is important and helpful since otherwise the patients have to pinch the stocking to adjust them and the pinching of these elastic units not only is difficult but can also pinch the skin as well. Even regular stockings may benefit from such tabs.

2. The unit may have an opening in the rear wall in the popliteal area so that it will prevent the gathering of material in that area to occur when the person bends the knee or sits down with the legs under him/herself.

3. Importantly the body of the unit may be made from a material such as screen so that it doesn't prevent the dissipation of perspiration and heat in the legs that makes many patients suffer and complain, especially in the hot season. These screens may have different sizes, thicknesses, openings and other important characteristics. These units may vary in order to allow the best model to be made. Also, the body of the unit or the elastic part may be made to have small holes of different sizes in order to allow the dissipation of the perspiration and heat to occur. The size of these openings in different areas may vary as well.

4. Importantly the body of the unit may be made to have only some areas of it made from a material such as a screen so to allow the dissipation of perspiration and heat in legs.

5. Importantly the body of the unit may be made to have areas or patches of open areas to allow the dissipation of perspiration and heat in legs.

6. The unit may be made to have an area of extra skin in front of the knee joint (please notice FIG. 10) in order to allow it to expand easily during the bending of the unit and give better feeling and durability to the unit.

7. This unit may also be made to have a ring made from soft material such as latex, rubber, sponge or similar material in order to be placed around the knee cap to hold it in place more securely.

8. This support unit may also have a series of extra and more protective pieces in the sides as shown at 50, 51, 52 in order to participate in holding and supporting the knee joint and/or the knee cap in place securely.

9. The extra pieces of this unit in the sides as shown at 50, 51, 52 can also be made adjustable as well, so that this will allow these pieces to be pulled off and stuck over the side again to have the tension of the wall adjusted. This can be done by having a piece of properly sized Velcro TM patch in the area under these pieces, so that the pieces 50, 51, and 52 can be moved away to be stuck again in a different distance over the support under them. Naturally, this will be the better choice.

10. In some models, the unit may be made to be more selective and give more options: for example, the user could decide the degree of the tension in the legs, so that at the times if the pressure was high, then the person could release the pressure. This will be done by having patches of Velcro TM fixed outside of the support (please notice FIG. 11) so that when needed the person can put on more or add some more support units to his/her leg. This will allow the original support to be less thick and then when the person needs to add more support to it. This will be a double support which will match each other.

11. These units may also have a zipper in front in order to allow them to be taken off or positioned in place easier. The zippers will bring the edges of these units together.

12. The units which bring the edges together such as the Velcro TM patches may also be further modified by a zipper as well in front or in the side in order to allow them to be opened or closed by the zipper if they wished to do so.

13. These units may also have a flap of the same elastic material or soft material in order to be placed and to stand under the open line between the borders of the elastic material in order to prevent any uncomfortable feeling or problems due to contact of the connection part with the skin, as shown at (a) in FIG. 5A.

Importantly the pieces of the velcro that are to be utilized to bring the edges of the stocking to each other can be made to be a separate unit as shown in FIGS. 6 and 7 or 8 and 9. They can be glued or fixed on the borders of a properly shaped elastic layer which has the proper size to make the elastic stockings. This method will facilitate the make up of these units significantly, and they can be fixed over the supportive stockings as mentioned above in the FIG. 7.

Also, some of such supportive units may be made to have a zipper in their front and side as the means of bringing the borders of the elastic layer together. A zipper can also be added to their other means of connection (such as velcro shown in FIG. 6 and 8) in order to allow the zipper to be used as an alternative means of bringing the edges of these units together. In some models the attachment piece shown at 6 & 7 or 8 & 9 may also have a zipper in their side before construction to allow it to be used.

Also importantly, a zipper may be made with the same mechanism shown for piece of 6 & 7 and 8 & 9 to have glued parts to allow them to be easily placed on the supportive stockings.

Importantly the different parts of the support unit and related parts may be made to have different sizes, thickness, elasticity, width, length, coloring, physical and chemical components. Also the important characteristics of these units may vary from model to model in order to allow different units to be made to satisfy different users.

One important advantage that can be added to these supportive stockings is to make them prevent phlebitis and blood clot formation in the legs in cases which the person would not have enough motion of the legs and body due to diseases, weakness, disabling conditions or lack of mobility. This kind of persistent immobility puts such patients among the very high risk group for development of blood clot formation in the veins of the legs and thigh. In some of them, the clots travel to the lungs and cause a condition called "Pulmonary Emboli." This condition is one of the sudden killers of the patients and a nightmare for doctors. Many attempts are made to move the debilitated patients; however, most of the times it is not successful when these patients are weak and are not motivated or forgetful to do the prescribed activity. In practice the supportive stockings are ordered and used many times but they would not prevent this problem in all cases when the main problem of the lack of activity still exists. But the fight should still be continued to make these patients move their extremities and overcome the weakness. For this reason this inventor introduces a complimentary unit to be used with these support stockings in order to increase their effectiveness and make a difference in such conditions. This will be a unit that will make the debilitated and non-active people increase the motion of their legs and thighs as well as diminish the chance of stagnant blood in the legs. This will be done with stimulation of their legs and body by one way or another as follows:

A1. In this method an electrical stimulator will be used in order to deliver a minute amount of electricity to the muscles of the legs in order to stimulate them to contract and naturally to move the blood in that area as well.

B1. In a similar method again an electrical stimulator will be used in order to cause a mechanical stimuli such a tickling sensation on the feet to move them.

C1. In this method the electrical stimuli will be used in order to work as a reminder to make the patients remember their own job to move their extremity to circulate their body.

D1. In this method the electrical stimuli may be in the form of visual stimuli such as blinking lights that can be placed in a convenient place such as the bottom of the bed or a similar place. This is in order to work as a reminder to the patient and make them to start the intermittent physical activity of their legs, breathing or body exercises, etc.

E1. These stimuli may be made to be in the form of sound stimuli of different forms; from beeping sounds to actual noise, etc. It will function as the needed stimuli and reminder to make the patients do their physical activity as prescribed for their legs, breathing or body etc. For example a recorder message from a patient's daughter may say: "Hi Dad, how are you? Did you do your activity? Don't forget them, get up and move. Do it for me. Christian." Or "Hi, Mom how are you? I hope you are doing well. Don't forget to do your leg exercises every 15 to 20 minutes."

F1. A combinations of these methods may also be used for the best results.

Importantly the support stocking and the units that will be used in these models will have openings in their walls to allow the connections between the electrode patches and the wiring of these units to be done properly. Also the wiring of these units will be made to be placed on the outside of these units in order to have a low profile and easily placed and tolerated. The support units will have a means of holding them in their walls such as proper attachments by sticking, gluing, snapping, stitching and any other proper connections.

The main unit to perform the function of this unit or the power pack and programer will be made from a mini computer that has a microchip which is powered by a battery. This unit will have the capacity to allow the unit to be planned to deliver the needed stimulus such as electrical stimuli in an intermittent and programed fashion in order to do the job. For example in the model A1 a minute amount of electricity will be intermittently released and taken by a series of wires to be delivered to the leg muscle via attachment of a proper electrodes no 61, 62 FIG. 13. This will make the muscles stimulated intermittently under an optional plan to prevent blood clot formation in that area. A similar model will also allow a unit which is mounted on a stand positioned in the lower end of the bed to do the job of stimulation. For example, it may create a motion to cause a tickling sensation in the sole of the legs to make the person to move the leg intermittently. Multiple other plans may also be chosen to reach this goal as well.

The power of presently available microchips and minicomputers has made it possible to use them in order to make multiple planning by a small unit, so that many uses may be made. They may be combined with lights, sound signals of any forms including recorders and voice players in order to made a very valuable units to reach the goals mentioned above. Such powerful microchips have made it possible to make such a powerful programmable control unit that will allow the program of such units to be chosen and factors such as frequency, space between the shocks, strength, the number and the nature of the units in use and other important factors of these stimulants to be controlled easily.

Importantly the different parts of the support unit and the other parts may be made to have different sizes, thickness, elasticity, width, length, coloring, physical and chemical components. Also the important characteristics of these units may vary from model to model in order to allow different units to be made to satisfy different users.

I claim:

1. An elastic leg support stocking comprising an elastic layer for wrapping around a leg to exert compressive force on a leg, and joining means for joining confronting marginal edges of said elastic layer that extend along the length of a leg when the elastic layer is wrapped therearound, said joining means comprising a first strip, a first portion of which is mounted on one of said confronting marginal edges and a second portion of which overlaps the other of said confronting marginal edges, said second portion of said first strip that overlaps said other of said confronting marginal edges comprising part of a hook and loop pile fabric material fastening system, said other of said confronting marginal edges comprising a part of a hook and loop pile fabric material (tm) fastening system that is complementary to the part of said hook and loop pile fabric material fastening system on said second portion of said strip, and a second strip that comprises a portion of a hook and loop pile fabric material fastening system that is the same as that on said second portion of said first strip, and that is separably adhered to said part of said hook and loop pile fabric material fastening system on said other of said confronting marginal edges to serve as an alignment guide for adhering said second portion of said first strip to said part of said hook and loop pile fabric material fastening system on said other of said confronting marginal edges.

2. An elastic leg support stocking as set forth in claim 1 in which said second strip is initially separably joined with said first strip at the time of initial application of said support stocking to a person's leg and upon initial application of the support stocking to a desired position is subsequently separated from said first strip.

3. An elastic leg support stocking as set forth in claim 1 in which said elastic layer extends from below a knee to above a knee and includes an opening in the popliteal area, and at least one pull tab is disposed to project from an edge of said opening.

* * * * *